United States Patent [19]

Hayes

[11] Patent Number: 5,549,685
[45] Date of Patent: Aug. 27, 1996

[54] AUGMENTATION FOR AN ORTHOPAEDIC IMPLANT

[75] Inventor: Kevin B. Hayes, Milford, Ind.

[73] Assignee: Zimmer, Inc., Warsawm, Ind.

[21] Appl. No.: 200,269

[22] Filed: Feb. 23, 1994

[51] Int. Cl.⁶ ........................................................ A61F 2/38
[52] U.S. Cl. ................................ 623/20; 623/11; 623/16; 623/18; 606/72; 606/73
[58] Field of Search .................................. 623/11, 16–18, 623/20; 606/60, 72–73

[56] References Cited

U.S. PATENT DOCUMENTS

| | | | |
|---|---|---|---|
| 4,911,721 | 3/1990 | Branemark et al. | 623/20 |
| 4,936,847 | 6/1990 | Manginelli | 623/20 |
| 4,936,853 | 6/1990 | Fabian et al. | 623/20 |
| 4,950,298 | 8/1990 | Gustilo et al. | 623/20 |
| 5,013,315 | 5/1991 | Barrows | 606/77 |
| 5,057,111 | 10/1991 | Park | 606/70 |
| 5,108,399 | 4/1992 | Eitenmuller et al. | 606/77 |
| 5,129,899 | 7/1992 | Small et al. | 623/13 |
| 5,152,797 | 10/1992 | Luckman et al. | 623/16 |
| 5,269,784 | 12/1993 | Mast | 606/73 |
| 5,346,492 | 9/1994 | Morgan | 606/60 |
| 5,380,323 | 1/1995 | Howland | 606/73 |

OTHER PUBLICATIONS

Biomet, Inc.–Maxim, The Complete Knee System–c1992.

Primary Examiner—David H. Willse
Assistant Examiner—P. Zuttarelli
Attorney, Agent, or Firm—Cary R. Reeves

[57] ABSTRACT

An augment for an orthopaedic implant contains a countersunk through hole. A fixation means interacts with the countersink to produce both downward and lateral forces on the augment. As the fixation means is tightened, it abuts one side of the countersink so that it exerts both a downward force and a lateral force on the augment. The lateral force causes the augment to press tightly against the implant. Because of the combination of downward and lateral forces, the augment strongly resists displacement and rotation.

9 Claims, 3 Drawing Sheets

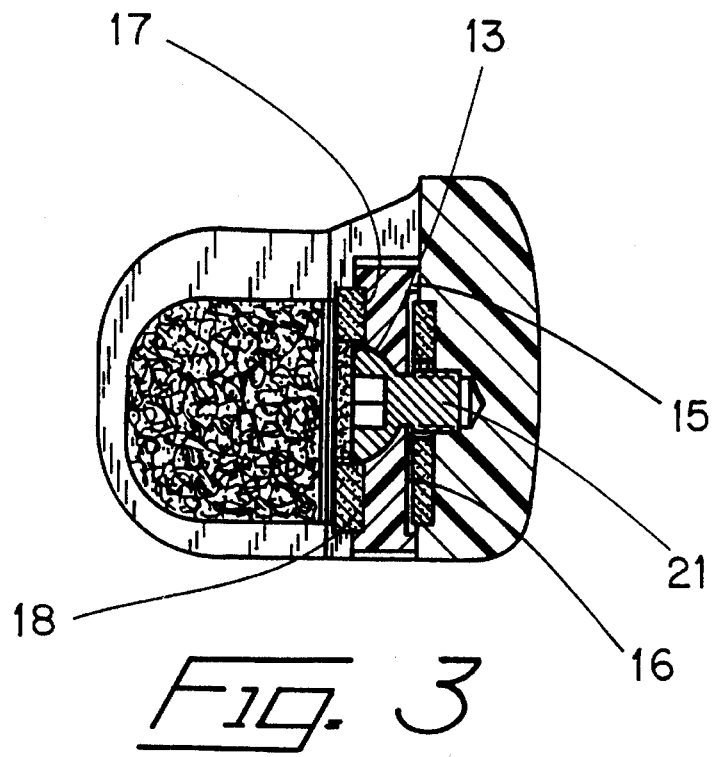
Fig. 3
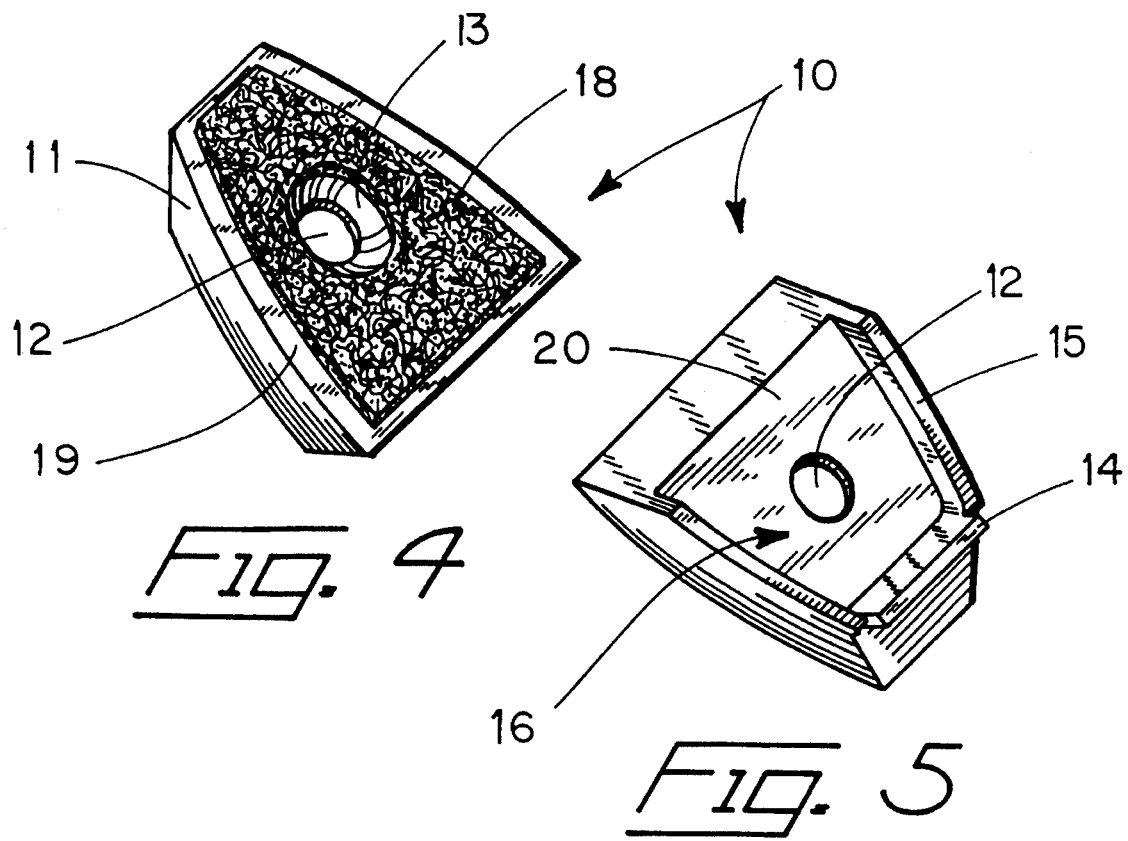
Fig. 4
Fig. 5

AUGMENTATION FOR AN ORTHOPAEDIC IMPLANT

BACKGROUND OF THE INVENTION

This invention relates to an orthopaedic implant intended for replacing a portion of a bone. More particularly, it relates to a means for augmenting such an implant so as to adapt the implant to fit a variety of situations.

In order to replace a defective portion of a bone, such as an arthritic joint, an orthopaedic surgeon cuts away the defective portion and shapes the remaining bone to a specific geometry. An implant, having bone contacting surfaces corresponding to this specific geometry, is then placed on the bone. The implant is typically either provided with a porous surface for the bone to attach to or it is cemented onto the bone.

Implants of this type, for a particular skeletal joint, are usually made available in a range of sizes to fit the varying sizes in the patient population. However, only a relatively small number of different sizes can practically be made available. Therefore, difficulties arise when a patient has a bone of an odd size or when the bone is abnormally shaped or deformed due to disease. Often, when a bone is shaped to the specific geometry to fit an implant, only a small area of the prepared bone will exhibit a deformity such as insufficient bone to support the implant. In such cases, implant augments have been successfully used to supplement the implant and fill the bone deficiency. These augments comprise small blocks or wedges of material that can be affixed to the implant. While augments have been generally successful, the various means of attaching them to the implant have been problematic. Prior augments have been attached using screws, cements and clips.

The challenge is to provide a strong, stable attachment with a minimum number of fastening elements that are easily employed. The attachment must resist linear as well as rotational forces and large separation forces as well as smaller forces causing slight relative motion between the augment and the implant. This slight relative motion, often referred to as micro-motion is problematic in that it can lead to wear debris from the augment and implant and it can prevent the growth of a solid bony interface adjacent the augment and implant.

SUMMARY OF THE INVENTION

The present invention provides for strong, stable attachment of an augment to an implant. The attachment is resistant to large separation forces as well as micro-motion and it is resistant to linear and rotational forces. In a preferred embodiment, the augment contains a countersunk through hole. The implant is provided with a threaded hole. A screw is used to attach the augment to the implant. With the augment positioned on the implant, the center of the countersink in the augment is not aligned with the center of the hole in the implant. Therefore when the screw is placed through the augment and threaded into the implant, the screw head abuts one side of the countersink so that as the screw tightens it exerts both a downward force and a lateral force on the augment. The lateral force causes the augment to translate until it contacts a structure on the implant which resists further translation. Further tightening of the screw causes the augment to press tightly against the implant both downwardly and laterally. Because of this combination of forces, the augment strongly resists displacement and rotation. In an alternative embodiment, lateral forces are created because the countersink is asymmetric.

BRIEF DESCRIPTION OF THE DRAWINGS

FIG. 3 is a sectional view taken along line A—A of FIG. 1.

FIG. 4 is an isometric view of the preferred embodiment of the augment showing the top.

FIG. 5 is another isometric view of the preferred embodiment of the augment showing the bottom.

DETAILED DESCRIPTION OF THE INVENTION

Figure 1:
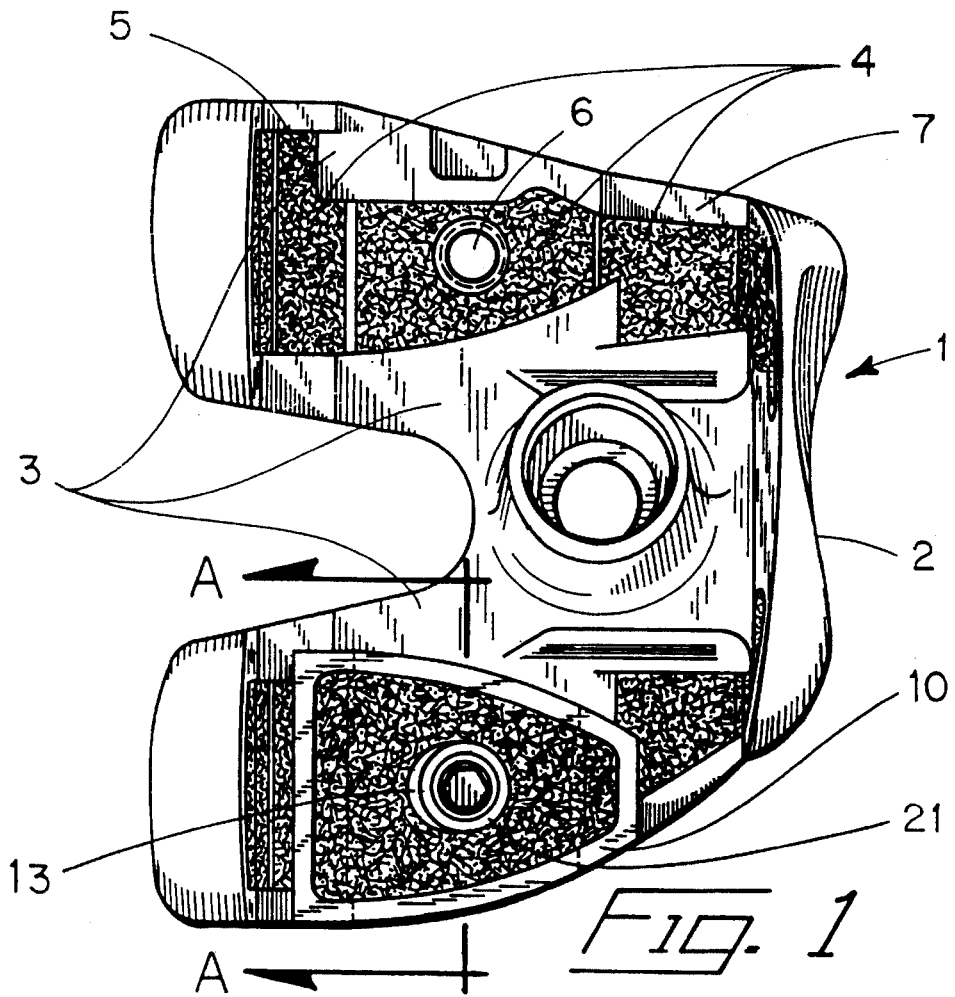
FIG. 1 is a plan view of the preferred embodiment of the invention.

In this description, a femoral component of a knee joint prosthesis has been chosen for illustrative purposes. The component is shown with an augment attached to one side and with another side adapted for receiving an additional augment. The invention is applicable to other augmented implants in addition to femoral knee implants.

Referring to FIGS. 1–5, an implant 1 has an articular surface 2 and an augment receiving surface 3. In a preferred embodiment, the augment receiving surface 3 contains a pocket area 4 for receiving porous surface material 5 or other provisions such as bone cement to enhance the attachment of the implant 1 to bone. Also in the preferred embodiment, a wall 7 is formed on the implant 1 adjacent the augment receiving surface 3. Finally, in the preferred embodiment, the implant 1 also has a threaded hole 6 in the augment receiving surface.

An augment 10 for attachment to the implant 1 comprises a body 11 having a top surface 19 and a bottom surface 20. A through hole 12 extends through the body from the top surface to the bottom surface. A countersink 13 is formed in the top surface 19 and communicates with the through hole 12. The preferred embodiment has a tab 14 extending from the body 11 of the augment 10 adjacent the through hole 12. The preferred embodiment also includes side rails 15 defining a recess 16. The preferred embodiment further includes an augment pocket 17 for receiving porous surface material 18 or other provisions such as bone cement to enhance the attachment of the augment to bone.

A screw 21 having a head with an undersurface 22 is preferably used to attach the augment 10 to the implant 1. The through hole 12 and countersink 13 are formed so that the screw 21 exerts a lateral force as well as a downward force on the augment.

Figure 2:
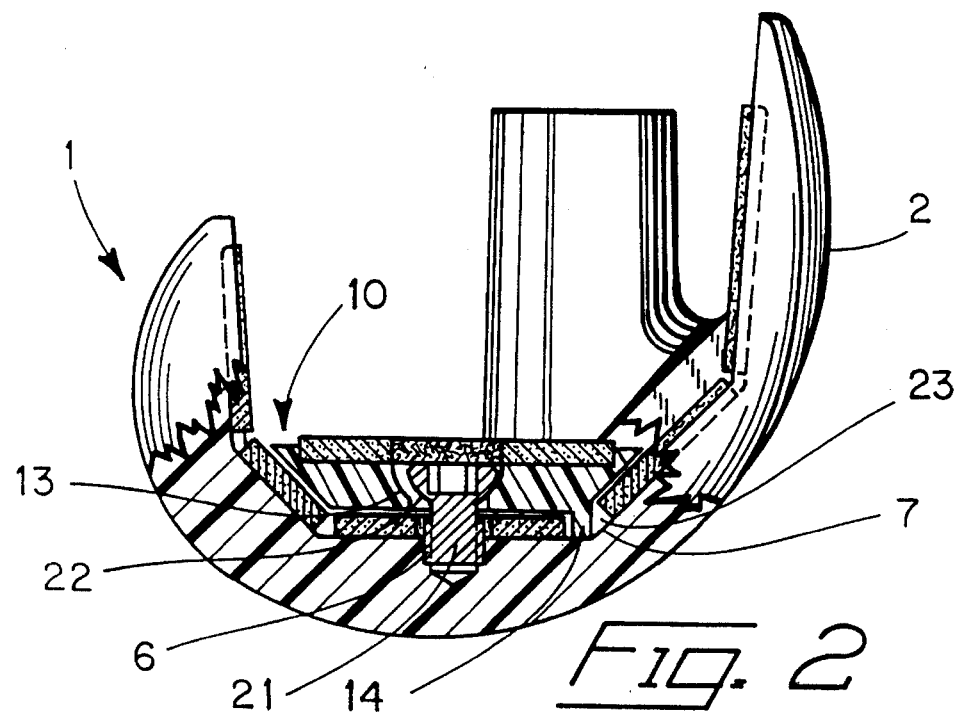
FIG. 2 is a partially sectioned side view of the preferred embodiment of FIG. 1.

In the preferred embodiment, shown in FIGS. 1–5, the lateral force results because the through hole and countersink are formed so that the screw 21 can pass through the augment 10 and thread into the threaded hole 6 when the center of the countersink 13 and the center of the threaded hole 6 are not in alignment. The purpose for this misalignment is so that the screw 21 can exert a lateral force on the augment 10 in addition to a downward force. In the illustrative embodiment the lateral force is directed toward the wall 7. The hole 12 has a length corresponding to the direction of the lateral force and a width perpendicular to the length. The countersink 13 has a similarly oriented length and width. In the preferred embodiment, the hole 12 and countersink 13 are elongated such that the length is greater than the width so that the screw fits closely along the sides, as shown in FIG. 3, and has clearance lengthwise, as shown in FIGS. 1 and 2.

Figure 6:
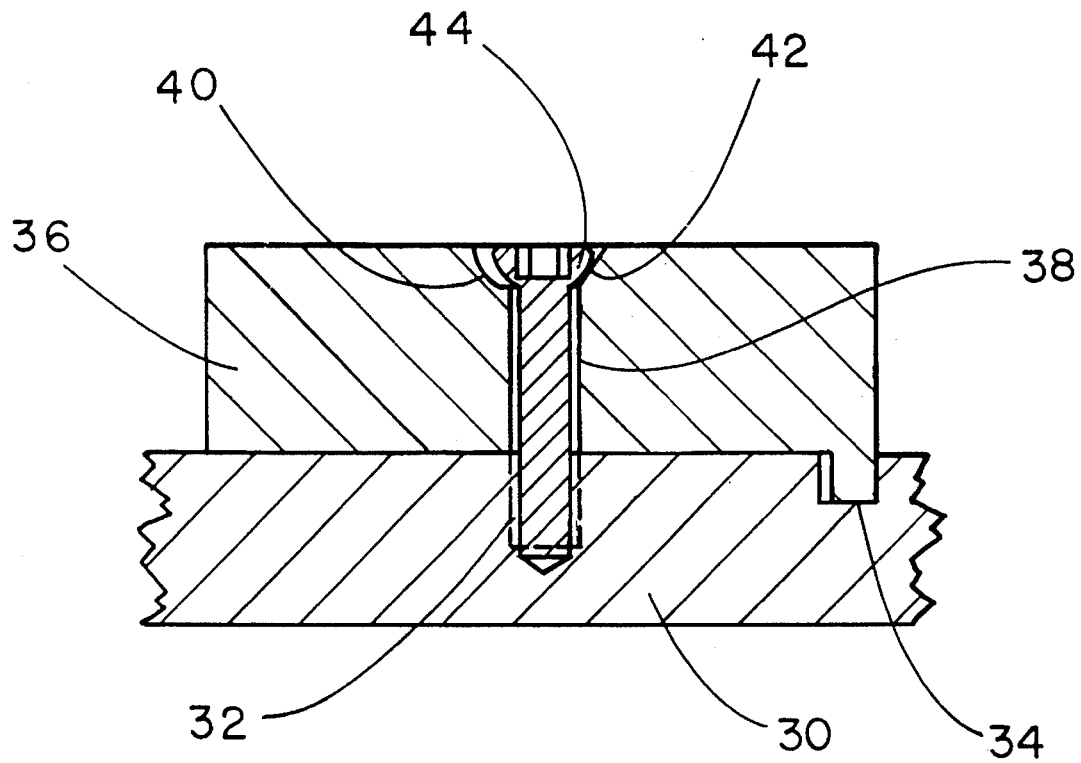
FIG. 6 is a cross sectional view of an alternative embodiment of the invention.
Figure 7:
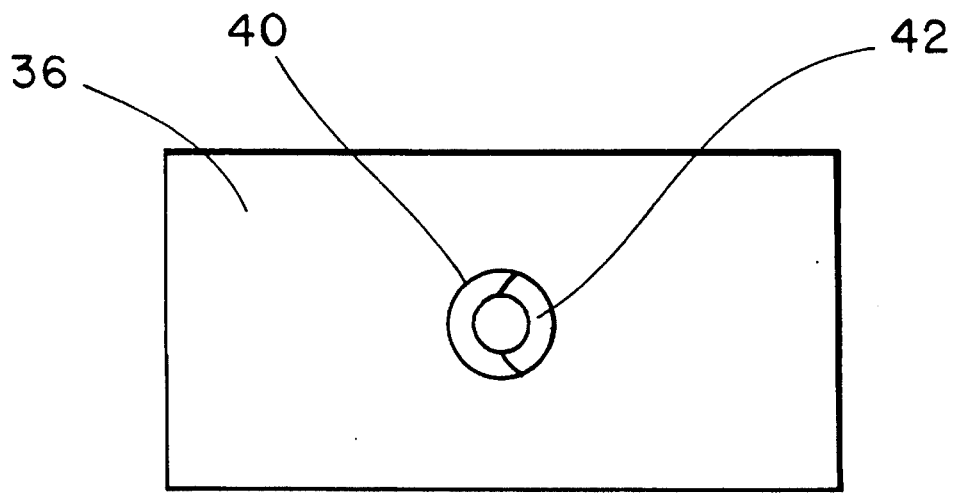
FIG. 7 is a top view of the augment of the alternative embodiment of FIG. 6.

In an alternative embodiment, shown in FIGS. 6 and 7, the lateral force results because the countersink is asymmetric. An implant 30 has a threaded hole 32 and a translation resisting means such as slot 34. The augment 36 has a through hole 38 and a countersink 40. The countersink 40 is asymmetric because of the oblique surface 42. Such an asymmetry is produced when less material is removed from a portion of the countersink or when material is added to a portion of the countersink. Because of surface 42, a screw 44 will contact one side of the countersink even when the axes of the screw 44, the countersink 40, the through hole 38 and the threaded hole 32 are in alignment as shown in FIG. 6.

In use, with respect to either the preferred embodiment or the alternative embodiment, the screw is placed through the augment and threaded into the threaded hole in the implant. The screw head abuts one side of the countersink. As the screw is tightened it exerts both a downward force and a lateral force on the augment. The augment contacts a structure on the implant, such as the wall 7 or slot 34, which resists translation by the augment. Further tightening of the screw causes the augment to press tightly against the implant both downwardly and laterally. This combination of forces resists both linear and rotational motion of the augment relative to the implant and results in secure fixation with a single screw.

In the preferred embodiment, the side rails 15 rest on the implant 1 astride the porous surface material 18. The recess 16 accommodates the porous surface material 18 to prevent contact between the porous surface material 18 and the augment 10. The tab 14 extends through a gap 23 in the porous surface material 18 so that when the screw 21 is tightened the tab 14 abuts the wall 7. In this preferred embodiment, therefore, the augment 10 is held tightly against the implant 1 and only contacts the implant 1 along the side rails 15 and the tab 14. The tab 14 is preferably rectangular.

The preferred embodiment comprises an elongated through hole 12 in the augment and an elongated countersink 13. However, a round countersink, one with equal length and width, would also work so long as the countersink 13, threaded hole 6, and translation resisting structure 7 on the implant 1 are aligned so as to produce a lateral force on the augment 10. Likewise, the hole could be round as long as it provides enough clearance to allow the augment to press tightly against the implant. Also, in the preferred embodiment, the countersink 13 and the undersurface 22 of the screw are spherical. However, any combination of undersurface 22 and countersink surfaces that will result in a lateral force when the screw is tightened will work and the countersink and undersurface contours need not necessarily be the same, as shown in the alternative embodiment of FIGS. 6 and 7.

The illustrated embodiments of this invention depict a screw and threaded hole for attaching the augment to the implant. Other fixation means could be used so long as they produce lateral forces in addition to downward forces. It will be understood by those skilled in the art that further variations in design and construction may be made to the preferred embodiment without departing from the spirit and scope of the invention defined by the appended claims.

What is claimed is:

1. An augment for attachment with a screw to an orthopaedic implant having a threaded hole, the augment comprising a body with a first surface and a second surface, the body having a through hole extending through the body from the first surface to the second surface and a countersink formed in the first surface communicating with the through hole, the through hole and countersink being shaped to allow the screw to pass through the through hole and thread into the threaded hole when the center of the countersink and the center of the threaded hole are not in alignment, the countersink having a spherical surface so that as the screw is tightened against the countersink surface a lateral force results tending to move the countersink into alignment with the threaded hole.

2. The augment of claim 1 wherein the through hole is elongated such that the through hole width is less than the through hole length and the countersink is elongated such that the countersink width is less than the countersink length.

3. The augment of claim 1 further including a tab extending downwardly from the second surface and perpendicular to the second surface.

4. The augment of claim 1 further including rails extending from the second surface, the rails defining a recess, the second surface forming the bottom of the recess.

5. An augmented orthopaedic prosthesis comprising:
   an implant having an augment receiving surface and a threaded hole formed in the augment receiving surface;
   a wall extending from the implant adjacent the augment receiving surface;
   an augment comprising a body with a first surface and a second surface, the body having a through hole extending through the body from the first surface to the second surface and a countersink formed in the first surface communicating with the through hole;
   a tab extending downwardly from the second surface and perpendicular to the second surface; and
   a screw having a head with an undersurface, the screw engageable with the through hole and threadably engageable witch the threaded hole,
   the through hole and countersink being located so that the center of the countersink and the center of the hole in the augment receiving surface are not in alignment when the augment is seated on the augment receiving surface and the tab is abutting the wall, the countersink and the undersurface being shaped so that as the screw is tightened the undersurface bears on the countersink resulting in a downward and a lateral force, the lateral force tending to move the countersink into alignment with the threaded hole and thus causing the tab to press tightly against the wall.

6. An augment for attachment to an orthopaedic implant, the augment comprising a body with a first surface and a second surface, the body having a through hole extending through the body from the first surface to the second surface and an asymmetric countersink formed in the first surface communicating with the through hole, the asymmetric countersink including an oblique surface on one side of the countersink.

7. An augmented orthopaedic implant assembly comprising:
   an implant;
   translation resisting means formed on the implant;
   an augment having a hole extending through it, the hole including a countersink; and
   fixation means cooperating with the countersink to produce both downward and lateral forces on the augment, the lateral force pressing the augment against the translation resisting means.

8. The implant assembly of claim 7 wherein the translation resisting means is a slot formed in a surface of the implant and the augment includes a tab extending downwardly from the augment, the tab and slot being in engagement so as to resist translation of the augment relative to the implant.

9. An augment for attachment with fixation means to an orthopaedic implant, the augment comprising a body having a hole extending through it, the hole including a countersink, the fixation means cooperating with the countersink to produce both downward and lateral forces on the augment, the lateral force pressing the augment against the implant.

* * * * *